United States Patent [19]
Stein et al.

[11] 3,943,178
[45] Mar. 9, 1976

[54] SECONDARY ALCOHOL ETHER ETHOXYLATES

[75] Inventors: Werner Stein, Erkrath-Unterbach; Wolfgang Rupilius, Hilden Rhineland; Peter Krings, Krefeld, all of Germany

[73] Assignee: Henkel & Cie GmbH, Dusseldorf-Holthausen, Germany

[22] Filed: June 11, 1974

[21] Appl. No.: 478,321

[30] Foreign Application Priority Data
June 18, 1973  Germany............................ 2331014

[52] U.S. Cl................ 260/615 B; 252/8.9; 252/94; 252/106; 252/121; 252/170; 252/351; 252/352; 252/353; 252/DIG. 1
[51] Int. Cl.$^2$................C07C 41/02; C07C 43/04; C07C 43/14
[58] Field of Search ................................ 260/615 B

[56] References Cited
UNITED STATES PATENTS

| | | | |
|---|---|---|---|
| 2,327,053 | 8/1943 | Marple et al..................... | 260/615 B |
| 2,870,220 | 1/1959 | Carter............................. | 260/615 B |
| 3,030,426 | 4/1962 | Moseley et al.................. | 260/615 B |
| 3,057,891 | 10/1902 | De Groote ..................... | 260/615 B X |
| 3,427,248 | 2/1969 | Lamberti et al.................. | 260/615 B |
| 3,489,690 | 1/1970 | Lachampt et al. ............... | 260/615 B |
| 3,511,676 | 5/1970 | Conn et al. ....................... | 106/280 |
| 3,637,869 | 1/1972 | Seizinger........................ | 260/615 B |

FOREIGN PATENTS OR APPLICATIONS

| | | | |
|---|---|---|---|
| 950,844 | 2/1964 | United Kingdom ............. | 260/615 B |
| 1,211,150 | 3/1960 | France | |

*Primary Examiner*—Howard T. Mars
*Attorney, Agent, or Firm*—Hammond & Littell

[57] ABSTRACT

Secondary alcohol ether ethoxylates having the formula

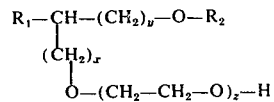

wherein $R_1$ is an aliphatic hydrocarbon radical with 4 to 18 carbon atoms, $R_2$ is an aliphatic hydrocarbon radical with 1 to 10 carbon atoms, $x$ and $y$ are integers 0 and 1, $z$ is an average value from 3 to 18, the sum of the carbon atoms of $R_1$ and $R_2$ is from 6 to 22 and the sum of $x + y$ is 1, as well as methods for their production and washing agent compositions containing them.

5 Claims, No Drawings

SECONDARY ALCOHOL ETHER ETHOXYLATES

OBJECTS OF THE INVENTION

An object of the present invention is the development of secondary alcohol ether ethoxylates having the formula

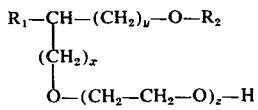

wherein $R_1$ is an aliphatic hydrocarbon radical having from 4 to 18 carbon atoms, $R_2$ is an aliphatic hydrocarbon radical having from 1 to 10 carbon atoms, $x$ and $y$ are integers 0 and 1, and $z$ is an average value between 3 and 18, with the proviso that the sum of the carbon atoms in $R_1$ and $R_2$ is from 6 to 22 and the sum of $x + y$ is 1.

Another object of the present invention is the development of a process for the production of the above secondary alcohol ether ethoxylates which comprises the steps of adding a 1,2-epoxy compound having the formula

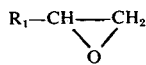

wherein $R_1$ is an aliphatic hydrocarbon radical having from 4 to 18 carbon atoms to an excess of at least twice the stoichiometric amount of an alcohol having the formula

wherein $R_2$ is an aliphatic hydrocarbon radical having from 1 to 10 carbon atoms with the proviso that the sum of the carbon atoms in $R_1$ and $R_2$ is from 6 to 22, in the presence of an etherification catalyst selected from the group consisting of alkali metal lower alkanolates and acidic etherification catalysts, under etherification conditions, removing the excess alcohol, reacting the desired amount $z$ of ethylene oxide with the resultant secondary alcohol ether in the presence of an alkali metal lower alkanolate alkoxylation catalyst under ethoxylation conditions, and recovering said secondary alcohol ether ethoxylates.

A further object of the present invention is the development of a process for washing textiles employing from 0.05 to 12 gm/l of the above secondary alcohol ether ethoxylates.

A yet further object of the present invention is the obtaining of washing agent compositions particularly for washing textiles containing from 0.5 to 30% by weight of the above secondary alcohol ether ethoxylates.

These and other objects of the present invention will become more apparent as the description thereof proceeds.

DESCRIPTION OF THE INVENTION

The above objects have been achieved by the development of novel interface-active ethoxylation products, a method for their production, and their use in washing and cleaning agents.

Essentially, the new ethoxylation products consist of secondary alcohol ether ethoxylates of Formula I

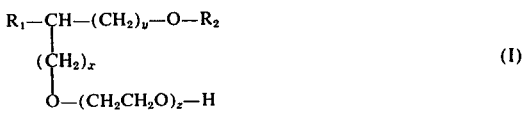

in which $R_1$ is an aliphatic hydrocarbon radical with 4 to 18 carbon atoms, $R_2$ is an aliphatic hydrocarbon radical with 1 to 10 carbon atoms, $x$ and $y$ are the numbers 0 and 1, and $z$ is a number between 3 and 18, preferably 5 and 15, the sum of the carbon atoms of $R_1$ and $R_2$ resulting in a number in the range from 6 to 22, and the sum $x + y$ always being 1.

Due to their excellent interface-active properties, the products according to the invention belong to the group of the non-ionic surface-active compounds; moreover, they have the properties of a graying inhibitor or soil suspension agent with textiles of natural and in particular synthetic fibers.

More particularly, the invention relates to secondary alcohol ether ethoxylates having the formula

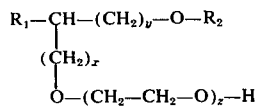

wherein $R_1$ is an aliphatic hydrocarbon radical having from 4 to 18 carbon atoms, $R_2$ is an aliphatic hydrocarbon radical having from 1 to 10 carbon atoms, $x$ and $y$ are integers 0 and 1, and $z$ is an average value between 3 and 18, with the proviso that the sum of the carbon atoms in $R_1$ and $R_2$ is from 6 to 22 and the sum of $x + y$ is 1.

Suitable as aliphatic hydrocarbon radicals $R_1$ and $R_2$ in Formula I are alkenyl and, preferably alkyl. The $R_1$ radicals preferably are straight-chain and the $R_2$ radical can be both straight-chain and branched-chain. Especially preferable are compounds of Formula I where $R_1$ and $R_2$ are straight-chain alkyl and the sum of the carbon atoms in $R_1$ and $R_2$ is a number in the range of from 10 to 18.

The compounds of Formula I are ethoxylation products of secondary hydroxy ethers or primary hydroxy ethers, depending on whether $x$ signifies the number 0 or 1. Of special practical interest are the compounds of Formula I in which $x = 0$ and $y = 1$, i.e. the ethoxylation products of a secondary hydroxy ether of the Formula Ia

wherein $R_1$, $R_2$ and $z$ have the above-assigned values.

The particular significance of the compounds of Formula Ia is based on the advantageous interface-active properties of these products in conjunction with their easy technical accessibility, which exists when $R_1$ represents an alkyl with 4 to 10 carbon atoms, and $R_2$ represents preferably primary alkyl with 4 to 8 carbon atoms, and $z$ is a number between 5 and 15, where the sum of the carbon atoms is $R_1$ and $R_2$ is in the range of from 10 to 18.

The properties and accessibility of the new substance of Formula I are predetermined in a particular manner by the selection of the starting compounds for their production. The invention therefore concerns also a method for the production of the secondary alcohol ether ethoxylates of Formula I, which comprises the steps of adding a 1,2-epoxy compound having the formula

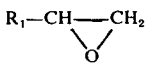

wherein $R_1$ is an aliphatic hydrocarbon radical having from 4 to 18 carbon atoms to an excess of at least twice the stoichiometric amount of an alcohol having the formula $R_2$ OH wherein $R_2$ is an aliphatic hydrocarbon radical having from 1 to 10 carbon atoms with the proviso that the sum of the carbon atoms in $R_1$ and $R_2$ is from 6 to 22, in the presence of an etherification catalyst selected from the group consisting of alkali metal lower alkanolates and acidic etherification catalysts, under etherification conditions, removing the excess alcohol, reacting the desired amount $z$ of ethylene oxide with the resultant secondary alcohol ether in the presence of an alkali metal lower alkanolate alkoxylation catalyst under ethoxylation conditions, and recovering said secondary alcohol ether ethoxylates.

More particularly, the preferable process for the production of the compounds of Formula I is characterized in that a 1,2-epoxy alkane of Formula II

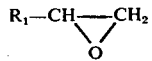 (II)

is added to an excess amount of an alcohol of Formula III $R_2$ OH (III)

wherein $R_1$ and $R_2$ have the meaning stated in Formula I, and to catalytic quantities of an alkali metal lower alkanolate, at a temperature of between 50° and 150°C, after the conversion of the epoxide to the ether, the excess alcohol is separated, and the residue is reacted, without further addition of catalyst, with ethylene oxide under elevated pressure, preferably in an inert gas atmosphere, until the calculated quantity of ethylene oxide is absorbed.

It is known from Malinovskii, "Epoxides and their Derivates", Jerusalem 1965, pp. 122 ff., that, in the alkali metal alcoholate-catalyzed reaction of a 1,2-epoxy alkane (II), with an alcohol (III), practically only the hydroxy ether with secondary alcohol group of Formula IV is formed

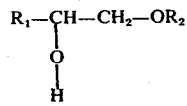 (IV)

It is further known that the ethoxylation of a secondary alcohol requires special technical expenditure in comparison with that of a primary alcohol. Thus, according to U.S. Pat. No. 2,870,220 to Carter, issued Jan. 20, 1959, a two-stage process must be employed utilizing first an acid catalyst and then an alkaline catalyst. According to U.S. Pat. No. 2,782,240 to Hefner et al., issued Feb. 19, 1957, the secondary alcohol must be used as an alkali metal alcoholate. According to British Patent No. 1,193,924, Henkel & Cie, issued June 3, 1970, trialkyl oxonium salts are necessary as catalysts for the alkoxylation of secondary alcohols. It was found, surprisingly, however, that the hydroxy ethers of Formula IV, produced by sodium alcoholate catalysts, can be reacted with ethylene oxide directly after removal of the excess alcohol, without isolation of the secondary hydroxy ether and without further addition of catalyst, there being obtained essentially the new substances of Formula Ia.

A special advantage of the process of the invention must be seen in that it is not necessary to isolate the intermediate phase of the β-hydroxy ether (IV) before the ethoxylation. Above all it is unnecessary to separate any by-products that might have formed, as for example the 2:1 adduct from 2 mols of epoxyalkane and 1 mol of alcohol forming in the reaction of the 1,2-epoxy alkane (II) with the alcohol (III) along with the 1:1 adduct of Formula IV. This by-product, formed in the above ratio, probably has the Formula V,

and may be contained in the technical β-hydroxy ether (IV) in as much as 20% by weight of the total quantity. The formation of the by-product (V) can, however, be suppressed in large measure by increasing the excess of alcohol (III).

Surprisingly, it has been found that the presence of the by-product of Formula V amounts of up to 20% by weight of the mixture of compounds to be ethoxylated is by no means disadvantageous and that the technical ethoxylation products of the invention, which are obtained with at least a two-fold excess and preferably with a three- to five-fold molar excess of the alcohol (III), have the same valuable properties as the purified ethoxylation product corresponding to Formula I. These products may be prepared by distillation of the secondary alcohol ether of Formula IV from the by-product residue. The purified secondary alcohol ether of Formula IV is then ethoxylated in the presence of an alkali metal alcoholate catalyst.

The products of Formula I according to the invention can be produced also by a second method. This method is characterized in that the condensation between the 1,2-epoxy alkane (II) and the at least two molar excess of the alcohol (III) is carried out in the presence of an acid etherification catalyst, preferably from the group of sulfuric acid, phosphoric acid, perchloric acid, and the fluorides and chlorides of boron, aluminum, iron, tin, titanium, antimony, and their ether complexes. After the separation of the excess alcohol and neutralization of the acid catalyst, and after addition of catalytic quantities of an alkali metal alcoholate, preferably an alkali metal lower alkanolate, the hydroxylated ether is reacted with ethylene oxide.

This method is employed when mixtures of the ethoxylation products of Formula I with different values for $x$ and $y$ are to be obtained, since in the acid-catalyzed etherification reaction of a 1,2-epoxy alkane (II) with an alcohol (III) a mixture of $\beta$-hydroxy ethers and $\alpha$-hydroxy methyl ethers is formed. The ratio of $\beta$-hydroxy ether to $\alpha$-hydroxy methyl ether being approximately 3:2 when $BF_3$-etherate is used as catalyst.

The special properties of the new secondary alcohol ether ethoxylates of Formula I, which are valid for the wide range of the radicals $R_1$ and $R_2$ of the definition, make it possible, by the proper selection of the starting compounds, to use especially those alcohols $R_2OH$ with 4 to 10 carbon atoms which usually occur as by-products in the technically known manufacturing processes for alcohols with more than 10 carbon atoms. What is here involved are primarily the so-called first distillate fatty acids with 4 to 10 carbon atoms which occur in the processing of natural fatty acid mixtures, or respectively the primary alcohols obtainable therefrom by reduction, as well as the $C_4$ to $C_{10}$ blends occurring in the production of synthetic fatty alcohols, for example, the alcohols obtainable by polymerization of ethylene with aluminum alkyls and subsequent oxidation and hydrolysis. But also the so-called oxo alcohols obtainable by hydroformylation of olefins can be utilized according to the method of the invention for the technically valuable products of Formula I.

Accordingly, for the method of the invention, for example, the following alcohols of Formula III are suitable: Methanol, ethanol, propanol, butanol, isobutanol, amyl alcohols, hexanol, octanol, 2-ethyl-hexanol, 3,5,5-trimethylhexanol, decanol, $C_4$-oxoalcohol (isomeric mixture), $C_6$ to $C_8$ first distillate fatty alcohols, $C_7$ to $C_9$ oxoalcohol (about 25% $\alpha$-alkyl branching).

The 1,2-epoxyalkanes of Formula II usable in the method of the invention are accessible in known manner by epoxidation of the respective terminal olefins. Examples of preferred usable epoxides are 1,2-epoxyhexane, 1,2-epoxyoctane, 1,2-epoxydecane, 1,2-epoxydodecane, and the $C_6$ to $C_{10}$-1,2-epoxides and $C_{11}$ to $C_{15}$-1,2-epoxides obtainable from terminal olefins as derived from cracking processes.

To obtain high yields of the ethoxylation product of Formula I it is necessary, as has been stated, to use the alcohol (III) in at least a two-fold excess, preferably in a quantity of 3 to 5 mols per mol of 1,2-epoxyalkane (II). The excess alcohol can easily be removed from the reaction medium again, such as by distillation. Because of this procedure, however, it is of interest to react an alcohol (III) of lowest possible boiling point with a 1,2-epoxyalkane (II), but as stated above, the sum of the carbon atoms from $R_1$ and $R_2$ should be a number in the range from 6 to 22, preferably a number in the range from 10 to 18.

The invention further relates to the use of the ethoxylation products of Formula I in washing and cleaning agent compositions which are present in solid form, as pastes, or as dispersions or solutions and comprise a content of at least one other active washing agent component from the group of the anionic and non-ionic surface-active agents and of the organic and inorganic builder salts. These washing and cleaning agent compositions are characterized in that they contain the ethoxylation products of Formula I in quantities of from 0.5 to 30% by weight.

If the washing agent compositions of the invention are solid, they are usually present as fine to granular powders, as agglomerates or granulates. Such preparations can be practically anhydrous, or they may contain water of crystallization or hydration. The preparations of the invention can be used also in pastes, dispersions, or solutions. These then contain smaller or larger amounts of solvents, such as water or water-soluble organic solvents, in which the other constituents are dissolved partially or completely. Thus, for certain cleaning purposes, solutions can be used which contain up to 1%, preferably up to 4%, by weight of the solid composition.

The invention therefore also relates to an improvement in the process for washing of textiles which comprises contacting soiled textiles with an aqueous solution containing surface-active compounds, builder salts and soil suspension agents for a time and at a temperature sufficient to disperse or dissolve said soil from said soiled textiles in said aqueous solution, separating said textiles, rinsing and drying said textiles and recovering cleaned textiles, the improvement consisting of employing from 0.05 to 12 gm/liter of the secondary alcohol ether ethoxylates of the invention, in said aqueous solution as part of said surface-active compounds and soil suspension agents.

Solid washing agents in which the ethoxylation products of Formula I can be used according to the invention are characterized by the following composition:

I. from 1 to 60% by weight of a tenside component consisting of
   a. from 15 to 50% by weight of the tenside component of the secondary alcohol ether ethoxylates of Formula I,
   b. from 50 to 85% by weight of the tenside component of anionic surface-active compounds and possibly other non-ionic surface-active compounds than those of a), II. from 40 to 99% by weight of organic and/or inorganic builder salts and, optionally, a bleaching component, and III. from 0 to 20% by weight of other common washing agent composition constituents such as optical brighteners, enzymes, soil suspension agents, textile softeners, antimicrobial agents, dyes, perfume and water.

The composition of the washing agents with a content of ethoxylation products of Formula I depends largely on the purpose of their use. Preparations which are used preferably as prewashing agent composition, as also the boiling or full washing agent compositions, have a pH of between 9.5 and 11 in 1% aqueous solution. This is usually obtained by a higher content of basic reacting builder salts. The preparations suitable as fine washing agent compositions are usually neutral to weakly alkaline (pH 7 to 9.5) in 1% aqueous solution, but sometimes weakly acid (pH 6 – 7). The boiling or full washing agent compositions differ from the other preparations also by their content of a bleaching component, which consists of a peroxy-compound as active oxygen carrier, in particular sodium perborate, stabilizers and possibly activators for the peroxy-compound, and which may amount to 10 to 40%, preferably 15 to 35%, by weight of the total washing agent. The stabilizers are employed in amounts of from 0 to 30% by weight of the bleaching component and the activators for the peroxy-compound are employed in amounts of from 0 to 40% by weight of the bleaching components.

The use according to invention of the secondary alcohol ether ethoxylates of Formula I in liquid cleaning agents is preferably in preparations of the following composition:

2 to 20% by weight of the secondary alcohol ether ethoxylates of Formula I,
1 to 20% by weight of sulfonate and/or sulfate surface-active compounds,
0 to 20% by weight of organic and/or inorganic builder salts,
40 to 97% by weight of water and possibly water-soluble organic solvents,
0 to 10% by weight of other common liquid washing agent constituents, such as solution aids, fat restoring agents, opacifiers, antimicrobial agents, perfume and dyes.

In the following, the other constituents contained in the washing and cleaning agent compositions besides the active substances according to the invention will be described in greater detail, arranged by substance class.

The anionic and non-ionic surface-active compounds or tensides contain in the molecule at least one hydrophobic organic moiety and one water-solubilizing, anionic or non-ionic group. The hydrophobic moiety is mostly an aliphatic hydrocarbon radical with 8 to 26, preferably 10 to 22 and particularly 12 to 18 carbon atoms or an alkyl aromatic radical, such as alkylphenyl, with 6 to 18, preferably 8 to 16 aliphatic carbon atoms.

Among the anionic surface-active compounds are, for example, soaps of natural or synthetic, preferably saturated, fatty acids, optionally, also, soaps of resinic or naphthenic acids. Suitable synthetic anionic tensides are those of the type of the sulfonates, sulfates and synthetic carboxylates.

Suitable anionic tensides of the sulfonate type are alkylbenzene sulfonates ($C_{9-15}$ alkyl) mixtures of alkenesulfonates and hydroxyalkanesulfonates, as well as alkanedisulfonates, as they are obtained, for example, from monoolefins with terminal or non-terminal double bonds by sulfonation with gaseous sulfur trioxide and subsequent alkaline or acid hydrolysis of the sulfonation products. Also suitable are alkanesulfonates which are obtained from alkanes by sulfochlorination or sulfoxidation and subsequent hydrolysis or neutralization or by bisulfite addition to olefins. Other suitable tensides of the sulfonate type are the esters of $\alpha$-sulfofatty acids, for example, the $\alpha$-sulfonic acids of hydrogenated methyl or ethyl esters of coconut, palmkernel or tallow fatty acids.

Suitable tensides of the sulfate type are the sulfuric acid monoesters of primary alcohols (e.g. from coconut fatty alcohols, tallow fatty alcohols or eleyl alcohol) and those of secondary alcohols. Also suitable are sulfated fatty acid alkanolamides, sulfated fatty acid monoglycerides or sulfated reaction products of 1 to 4 mols of ethylene oxide with primary or secondary fatty alcohols or alkylphenols.

Other suitable anionic tensides are the fatty acid esters or amides of hydroxy- or amino-carboxylic acids or sulfonic acids, such as the fatty acid sarcosides, fatty acid glycolates, fatty acid lactates, fatty acid taurides or fatty acid isoethionates.

The anionic tensides can be present in the form of their alkali metal salts, such as the sodium or potassium salts, the ammonium salts, as well as soluble salts of organic bases, such as the lower alkylolamines, for example, mono-, di- or triethanol amine.

Suitable non-ionic surface-active compounds or tensides are the addition products of 4 to 40, preferably 4 to 20 mols of ethylene oxide to 1 mol of a fatty alcohol, alkylphenol, fatty acid, fatty amine, fatty acid amide or alkanesulfonamide. Particularly important are the addition products of 5 to 16 mols of ethylene oxide to coconut fatty alcohols or tallow fatty alcohols, to oleyl alcohol or to secondary alkanols with 8 to 18, preferably 12 to 18 carbon atoms, as well as monoalkylphenols or dialkylphenols with 6 to 14 carbon atoms in the alkyls. In addition to these water-soluble non-ionics, polyglycol ethers with 1 to 4 ethylene glycol ether radicals in the molecule, which are insoluble or not completely water-soluble, are also of interest, particularly if they are used together with water-soluble non-ionic or anionic tensides.

Furthermore, the water-soluble addition products of 20 to 250 mols of ethylene-oxide to polyoxypropylene glycol containing 10 to 100 propylene glycol ether groups (Pluronics), to alkylenediamine-polyoxypropylene glycol (Tetronics), and to alkylpolyoxypropylene glycols with 1 to 10 carbon atoms in the alkyl chain, can also be used where the polyoxypropylene glycol chain acts as a hydrophobic radical.

Non-ionic tensides of the type of the amine oxides or sulfoxides can also be used.

The foaming power of the tenside can be increased or reduced by combination of suitable tenside types. A reduction can also be achieved by additions of non-surface-active organic substances.

Suitable foam stabilizers, particularly in tensides of the sulfonate or sulfate type, are surface-active carboxy or sulfobetaines, as well as the above-named non-ionics of the alkylolamide type. Moreover, fatty alcohols or higher terminal diols have been suggested for this purpose.

A reduced foaming power, that is desirable for the use in washing machines, is often attained by combination of different tenside types, such as of sulfates and/or sulfonates with nonionics, and/or with soaps. In soaps, the foam inhibition increases with the degree of saturation and the number of carbons in the fatty acid residue. Soaps derived from saturated $C_{20-24}$ fatty acids have been proven good as foam inhibitors.

The non-tenside foam inhibitors included N-alkylated aminotriazines, optionally containing chlorine, which are obtained by the reaction of 1 mol of cyanuric acid chloride with 2 to 3 mols of a mono- and/or dialkylamine with 6 to 20, preferably 8 to 18 carbon atoms in the alkyl radicals. Similarly effective are propoxylated and/or butoxylated aminotriazines, such as, products that are obtained by the addition of from 5 to 10 mols of propylene oxide to 1 mol of melamine and further addition of from 10 to 50 mols of butylene oxide to this propylene-oxide derivative.

Likewise suitable as non-tenside foam inhibitors are water-insoluble organic compounds, like paraffins, or halogenated paraffins with melting points below 100°C, aliphatic $C_{18}$ to $C_{40}$ ketones, as well as aliphatic carboxylic acid esters which contain in the acid or alcohol residue, optionally, also in both of these residues, at least 18 carbon atoms (such as triglycerides or fatty acid/fatty alcohol esters). These compounds can be used to reduce foaming, particularly in combinations of tensides of the sulfate and/or sulfonate type with soaps.

Particularly low-foaming non-ionics, which can be used either alone or in combination with anionic, amphoteric and non-ionic tensides, and which reduce the foaming power of high-foaming tensides, are the addition products of propylene oxide on the above-described surface-active polyoxyethylene-glycol ethers as well as the likewise-described addition products of ethylene oxide to polyoxypropylene glycols and to alkylenediamine polyoxypropylene glycols or to alkyl polyoxypropylene glycols having 1 to 10 carbons in the alkyl.

Weakly acid, neutral or alkaline-reacting inorganic or organic salts can be used as builder salts. The builder salts are salts capable of complexing calcium ions or precipitating them, preferably the salts are the alkali metal salts.

Of special importance are the inorganic salts capable of complexing or sequestering calcium, such as the water-soluble alkali metal condensed phosphates, such as the alkali metal metaphosphates or alkali metal polyphosphates, in particular pentasodium tripolyphosphate. These phosphates may be replaced wholly or partially by organic builder salts capable of complexing calcium ions, preferably the alkali metal salts. These organic sequestering agents include compounds of the following classes:

1. The aminopolycarboxylic acids, such as amino-lower-alkanoic acids and polyamino-lower-alkane-poly-lower-alkanoic acids, for example, nitriloacetic acid, ethylenediaminetetraacetic acid, diethylenetriaminepentaacetic acid, as well as higher homologs.

2. The lower alkane polyphosphonic acids, such as methane diphosphonic acid.

3. The amino- and hydroxy-substituted alkane polyphosphonic acids, having 1 to 9 carbon atoms, such as 1-aminoethane-1,1-diphosphonic acid, amino-tri-methylenephosphonic acid, methylamino- or ethylamino-di-methylenephosphonic acid, ethylene diaminetetra-methylenephosphonic acid, dimethylaminomethane-1,1-diphosphonic acid, 1-hydroxyethane-1,1-diphosphonic acid, etc.

4. The phosphonoalkane polycarboxylic acids with 1 and 2 phosphono and 2 and 3 carboxyl groups and 4 to 9 carbon atoms, such as 1-phosphonoethane-1,2-dicarboxylic acid, 2-phosphonopropane-2,3-dicarboxylic acid, 1,1-diphosphonopropane-2,3-dicarboxylic acid, 2-phosphonobutane-1,2,4-tricarboxylic acid, 2-phosphonobutane-2,3,4-tricarboxylic acid, etc.

Of special importance are the nitrogen-free and phosphorus-free polycarboxylic acids forming complex salts with calcium ions, which include also carboxyl group-containing polymers. These organic sequestering agents, particularly in the form of their alkali metal salts include compounds of the following classes:

5. Hydroxyalkanepolycarboxylic acids having from 4 to 12 carbon atoms and cyclic polycarboxylic acids having from 4 to 12 carbon atoms, such as citric acid, tartaric acid, benzenehexacarboxylic acid and tetrahydrofurantetracarboxylic acid.

6. 2,2'-hydroxydisuccinic acid and carboxymethyloxysuccinic acid.

7. The carboxymethylated, polyhydric $C_2$ to $C_6$ alcohols and $C_3$ to $C_6$ hydroxycarboxylic acids, containing at least two carboxyl groups in the molecule, preferably the carboxymethyl derivatives of alkanepolyols having 2 to 6 carbon atoms and hydroxyalkane - carboxylic acids having 3 to 6 carbon atoms, such as the compounds: dicarboxymethyl-ethylene glycol and dicarboxymethyl-diethylene glycol, tricarboxylmethyl-glycerine, mono- and di-carboxymethyl-glyceric acid, carboxymethyl-tartronic acid, carboxymethyl-methyl-tartronic acid, carboxymethyl-maleic acid, mono- and di-carboxymethyl-tartaric acid, also the carboxymethylated derivates of glutaric acid, saccharic acid, mucic acid, gluconic acid, the erythritols, pentaerythritol, 2,2-dihydroxymethyl-propanol, sorbitol, mannitol, xylitol, etc.

8. The polymeric carboxylic acids with molecular weights over 350, and at least one carboxyl group per each molecular weight unit of 175, such as polyacrylic acid, poly-α-hydroxyacrylic acid, the polycarboxylic acids obtained from mixed polymerization of maleic acid anhydride with ethylene or propylene, isobutylene or styrene, or with vinyl methyl ether or furan, or with acrylic acid, as well as the polyhydroxy-carboxylic acids obtained from acrolein and acrylic acid with $H_2O_2$ and the Cannizzaro reaction, etc.

Other builder salts, which because of their hydrotropic properties, are usually utilized in liquid compositions are the alkali metal salts of organic non-surface-active sulfonic acids, carboxylic acids and sulfocarboxylic acids containing from 2 to 9 carbon atoms. These include, for example, water-soluble alkali metal salts of alkanesulfonic acid, benzenesulfonic acid, toluenesulfonic acid, or xylenesulfonic acid or cumenesulfonic acid, water soluble alkali metal salts of sulfoacetic acid, sulfobenzoic acid, sulfophthalic acid or of succinic acid as well as the corresponding salts of acetic acid or lactic acid. In addition, as further solution aids, acetamide and urea may be employed.

In addition to the active secondary alcohol ether ethoxylates of Formula I according to the invention, additional soil suspension agents or dirt carriers may be employed, which keep the dirt released from the fibers in suspension in the liquor and so prevent graying. Suitable compounds are water-soluble colloids, mostly of an organic nature, such as the water-soluble salts of polymeric carboxylic acids, glue, gelatin, salts of ether carboxylic acids or ether sulfonic acids of starch or cellulose, or salts of acid sulfuric acid esters of cellulose or starch. Water-soluble polyamides containing acid groups are also suitable for this purpose. Furthermore, soluble starch preparations and other than the above-mentioned starch products can be used, for example, degraded starches, aldehyde starches, etc. Polyvinyl pyrrolidone can also be used.

Among the compounds serving as bleaching agents and releasing $H_2O_2$ in water, sodium perborate tetrahydrate ($NaBO_2$. $H_2O_3$. 3 $H_2O$) and the monohydrate ($NaBO_2$. $H_2O_2$) are of particular importance. But also other $H_2O_2$ releasing borates can also be used, such as perborax $Na_2B_4O_7$. 4 $H_2O$. These compounds can be replaced partly or completely by other carriers of active oxygen, particularly by peroxyhydrates, such as peroxycarbonates, ($Na_2CO_3$ . 1.5 $H_2O_2$), peroxypyrophosphates, citrate perhydrates, urea-$H_2O_2$ compounds, as well as by $H_2O_2$-releasing peracid salts, such as Caroates ($KHSO_5$), perbenzoates or peroxyphthalates.

It is recommended to incorporate water-soluble and/or water-insoluble stabilizers for the peroxy compounds together with the latter in amounts of 0.25 percent to 10% by weight. Water-insoluble stabilizers, which amount to 1 to 8%, preferably 2 to 7% of the weight of the entire preparation are, for example, the magnesium having a $MgO$ : $SiO_2$ ratio of 4:1 to 1:4, preferably 2:1 to 1:2, and particularly 1:1, which are mostly obtained by precipitation from aqueous solutions. In their place, other alkaline earth metal, cadmium or tin silicates of corresponding compositions are also usable. Also hydrous oxides of tin are suitable as stabilizers. Water-soluble stabilizers, which can be present together with water-insoluble stabilizers, are mostly the organic sequestering agents which can be added in amounts of 0.25 to 5%, preferably 0.5 to 2.5% of the weight of the entire preparation.

In order to obtain a satisfactory bleaching effect when washing at temperatures below 80°C, particularly in the range of 60° to 40°C, activator-containing bleaching components are preferably incorporated in the preparations.

Certain N-acyl and/or O-acyl compounds forming, with $H_2O_2$, organic per acids serve as activators for per compounds releasing $H_2O_2$ in water. Particularly to be mentioned are acetyl, propionyl or benzoyl compounds, as well as carbonic acid or pyrocarbonic acid esters. Suitable compounds are among others: the N-diacylated and N,N'-tetraacylated amines, such as N,N,N',N'-tetraacetyl-methylenediamine, N,N,N',N'-tetraacetyl-ethylenediamine, N,N-diacetyl-aniline and N,N-diacetyl-p-toluidine, or the 1,3-diacylated hydantoins and alkyl-N-sulfonyl-carbonamides, such as N-methyl-N-mesyl-acetamide, N-methyl-N-mesyl-benzamide, N-methyl-N-mesyl-p-nitrobenzamide, and N-methyl-N-mesyl-p-methoxybenzamide, the N-acylated cyclic hydrazides, acylated triazoles or urazoles, such as monoacetyl maleic acid hydrazide, the O,N,N-trisubstituted hydroxylamines, such as O-benzoyl-N,N-succinyl-hydroxylamine, O-acetyl- N,N-succinyl-hydroxylamine, O-p-methoxybenzoyl-N,N-succinyl-hydroxylamine, O-p-nitrobenzoyl-N,N-succinyl-hydroxyamine and O,N,N-triacetyl-hydroxylamine, the N,N'-diacyl-sulfuryl-amides, such as N,N'-dimethyl-N,N'-diacetyl-sulfurylamide, and N,N'-diethyl-N,N'-diethyl-N,N'-dipropionyl-sulfuryl amide, the triacyl cyanurates, such as triacetyl cyanurate or tribenzoyl cyanurate, the carboxylic acid anhydrides, such as benzoic acid anhydride, m-chlorobenzoic acid anhydride, phthalic acid anhydride, 4-chlorophthalic acid anhydride, the sugar esters, such as glucose pentaacetate, the 1,3-diacyl-4,5-diacyloxyimidazolidines, for example the compounds 1,3-diformyl-4,5-diacetoxy-imidazolidine, 1,3-diacetyl-4,5-diacetoxy-imidazolidine, 1,3-diacetyl-4,5-dipropionyloxy-imidazolidine, the acylated glycolurils, such as tetrapropionyl glycoluril or diacetyl-dibenzoyl glycoluril, the diacylated 2,5-diketopiperazines, such as 1,4-diacetyl-2,5-diketopiperazine, 1,4-dipropionyl-2,5-diketopiperazine, 1,4-dipropionyl-3,6-dimethyl-2,5-diketopiperazine, the acetylated or benzolylated products of propylenediurea or 2,2-dimethyl-propylene diurea [2,4,6,8-tetraazabicyclo-(3,3,1)-nonane-3,7-dione or its 9,9 dimethyl derivative], and the sodium salts of p-ethoxycarbonyloxy)-benzoic acid and p-(propoxycarbonyloxy)-benzene sulfonic acid.

The activated chlorine compounds serving as bleaching agents can be of an inorganic or organic nature.

The inorganic active chlorine compounds include alkaline metal hypochlorites, which can be used particularly in the form of their mixed salts or addition compounds with orthophosphates or on condensed phosphates such as with alkali metal pyrophosphates and polyphosphates, or with alkali metal silicates. If the washing agents and washing assistant compositions contain mono-persulfates and chlorides, active chlorine is formed in aqueous solution.

The organic active-chlorine compounds which can be used are particularly the N-chloro compounds, where one or two chlorine atoms are linked to a nitrogen atom, the third valence of the nitrogen atoms leading preferably to a negative group, particularly to a CO— or $SO_2$—group. These compounds include dichlorocyanuric acid and trichlorocyanuric acid or their salts, chlorinated alkylguanides or alkylbiguanides, chlorinated hydantoins and chlorinated melamines.

The washing agents can contain optical brighteners such as those for cotton, particularly derivatives of diaminostilbenedisulfonic acid or its alkali metal salts. Suitable are, for example, salts of 4,4'-bis-(2-anilino-4-morpholino-1,3,5-triazin-6-yl-amino)-stilbene-2,2'-disulfonic acid or similarly compounds which have instead of the morpholino group, a diethanolamino group, a methylamino group or a 2-methoxyethylamino group. Brighteners for polyamide fibers which can be used are those of the type of the 1,3-diaryl-2-pyrazolines, for example, the compound 1-(p-sulfamoyl-phenyl)-3-(p-chlorophenyl)-2-pyrazoline, as well as compounds of similar composition which have instead of the sulfamoyl group, for example, the methoxycarbonyl group, the 2-methoxyethoxycarbonyl group, the acetylamino group or the vinylsulfonyl group. Suitable polyamide brighteners are also the substituted aminocumarins, for example, 4-methyl-7-dimethylamino-cumarin or 4-methyl-7-diethylaminocumarin. Furthermore, the compounds 1-(2-benzimidazolyl)-2-(1-hydroxyethyl-2-benzimidazolyl)-ethylene and 1-ethyl-3-phenyl-7-diethylamino-carbostyril can also be used as polyamide brighteners. Brighteners for polyester and polyamide fibers which can be used are the compounds 2,5-di-(2-benzoxazolyl)-thiophene,2-( 2benzoxazolyl)-naphtho-[2,3-b]-thiophene and 1,2-di-(5-methyl-2-benzoxazolyl)-ethylene. Furthermore, brighteners of the type of the substituted 4,4'-distyryl-diphenyls can be utilized, for example, the compound 4,4'-bis-(4-chloro-3-sulfostyryl)-diphenyl. Mixtures of the above-mentioned brighteners can likewise be used.

The enzyme preparations to be used are mostly a mixture of enzymes with different effects, such as proteases, carbohydrases, esterases, lipases, oxidoreductases, catalases, peroxidases, ureases, isomerases, lyases, transferases, desmolases, or nucleases. Of particular interest are the enzymes, obtained from bacteris strains or from fungi, such as Bacillus subtilis or Streptomyces griseus, particularly proteases and amylases, which are relatively stable towards alkalis, percompounds, and anionic tensides and are still effective at temperatures up to 70°C.

Enzyme preparations are marketed by the manufacturers mostly as aqueous solutions of the active substances or as powders, granulates or as cold-sprayed products. They frequently contain sodium sulfate, sodium chloride, alkali metal ortho-, pyro- and polyphosphates, particularly tripolyphosphate, as fillers. Dust-free preparations are particularly valued. These are obtained in a known manner by incorporating of oily or pasty nonionics or by granulation with the aid of melts of water-of-crystallization-containing salts in their own water-of-crystallization.

Enzymes may be incorporated which are specific for certain types of soil, for example, proteases or amylases or lipases. Preferably, combinations of enzymes with different effects are used, particularly combinations of proteases and amylases.

The organic solvents utilized in the liquid washing agent compositions of the invention as liquid carriers are water-soluble or emulsifiable with water, aliphatic organic solvents having no more than 7 carbon atoms, particularly alkanols and alkanediols having from 1 to 5 carbon atoms, esters thereof with alkanoic acids having no more than 4 carbon atoms and ethers thereof with hydroxyalcohols having no more than 4 carbon atoms, for example, methanol, ethanol, propanol, isopropanol, butanol, amyl alcohol, ethylene glycol, diethylene glycol, triethylene glycol, propylene glycol, butylene glycol, ethyl acetate, etc. In addition alkanones having 3 to 7 carbon atoms may be employed, such as acetone and methylethyl ketone. The water-soluble solvents are preferred.

In addition, where required to give the desired pH of the 1% aqueous solution of the washing compositions of the invention, water-soluble inorganic wash alkalis are employed. These wash alkalis are the bicarbonates, carbonates, borates or silicates of the alkali metals, and alkali metal sulfates.

Suitable antimicrobial substances with a bactericidal, bacteriostatic or fungicidal or fungistatic action and which are water-soluble as such or in the form of their salts can be employed in the powdery compositions of the invention. Among these are the quaternary ammonium compounds which contain in the molecule one long-chained aliphatic and two short-chained aliphatic hydrocarbon radicals, and an aromatic organic radical linked over an aliphatic carbon atom with the nitrogen atoms, or an aliphatic radical with double bonds, such as dimethyl-benzyldodecyl ammonium chloride or dibutyl-allyl-dodecyl ammonium chloride. Suitable active substances are also the bromo and nitro substituted alkanols and alkanediols having 3 to 5 carbon atoms, for example, 2-bromo-2-nitropropane-1,3-diol, 1-bromo-1-nitro-3,3,3-trichloro-2-propanol, 2-bromo-2-nitro-butanol, as well as phenolic compounds of the type of the halogenated phenols, the halogenated alkylphenols, halogenated cycloalkylphenols, halogenated aralkylphenols, and halogenated phenylphenols, the halogenated alkylene bisphenols, the halogenated hydroxybenzoic acid derivatives, and the preferably halogen-substituted phenoxyphenols, such as 2-hydroxy-2',4,4'-trichloridiphenyl ether. Suitable for preservation of the liquid preparations as antimicrobial substances are also, for example, formaldehydes as an aqueous solution, benzoic acid, salicylic acid and sorbic acid.

The following examples are illustrative of the practice of the invention without being limitative in any respect.

EXAMPLES

EXAMPLE 1

2-Hydroxydecyl-n-butyl ether + 10 EO 0.46 gm (0.02 gm-atom) of sodium were added to 185 gm (2.5 mols) of n-butanol. After dissolution of the sodium, the temperature was raised to 100°C, and an amount of 78.2 gm (0.5 mol) of 1,2-epoxy decane was added in drops within 30 minutes while stirring. The reaction mixture was maintained at 100°C for 4 hours. Then the excess alcohol was distilled, and by subsequent vacuum distillation at 100° to 120°C and 0.06 Torr . the 2-hydroxy-decyl-n-butyl ether was separated from the higher boiling by-product. In this manner the intermediate product 2-hydroxydecyl-n-butyl ether (refractive index $n_D^{20} = 1.4392$) was obtained in a yield of 87%.

For ethoxylation 230 gm (1 mol) of the intermediate product were admixed with 2.8 gm of sodium methylate in an autoclave and reacted under a nitrogen atmosphere at 130° to 140°C with 440 gm (10 mols) of ethylene oxide. The ethylene oxide was forced over in portions with nitrogen, and the pressure was increased stepwise so that the temperature in the reactor was maintained at 130° to 140°C. After 5 hours, the total amount of ethylene oxide charged was absorbed. The ethoxylation product according to the invention, thus obtained, 2-hydroxydecyl-n-butyl ether + 10 EO (ethylene oxide units), was characterized by a hydroxyl number of 95 and a cloud point of 58° to 62°C.

In a similar manner the active secondary alcohol ether ethoxylates according to the invention, as listed in Table I, were produced on the basis of the pure intermediate product.

TABLE I

| Example | Active Substance | Formula 1 where y = 1 and x = 0 | | | | | Carbon Atoms $R_1 + R_2$ |
|---|---|---|---|---|---|---|---|
| | | Hydroxyl number | Cloud point in °C | $R_1$ | $R_2$ | z | |
| 1 | 2-Hydroxydecyl-n-butyl ether + 10 EO | 95 | 58–62 | octyl | butyl | 10 | 12 |
| 2 | 2-Hydroxyoctyl-hexyl ether + 10 EO | 90 | 60 | hexyl | hexyl | 10 | 12 |
| 3 | 2-Hydroxyhexyl-octyl ether + 10 EO | 93 | 60–61 | butyl | octyl | 10 | 12 |
| 4 | 2-Hydroxyhexyl-2-ethyl-hexyl ether + 10 EO | 92 | 60–64 | butyl | 2-ethyl-hexyl | 10 | 12 |
| 5 | 2-Hydroxydecyl-isobutyl ether + 10 EO | 90 | 64 | octyl | iso-butyl | 10 | 12 |
| 6 | 2-Hydroxydecyl-butyl ether + 5 EO | 125 | | octyl | butyl | 5 | 12 |
| 7 | 2-Hydroxydecyl-butyl ether + 7 EO | 109 | | octyl | butyl | 7 | 12 |
| 8 | 2-Hydroxydodecyl-ethyl ether + 10 EO | 88 | | decyl | ethyl | 10 | 12 |
| 9 | 2-Hydroxytetradecyl-methyl ether + 11 EO | | | dodecyl | methyl | 11 | 13 |
| 10 | 2-Hydroxydecyl-decyl ether + 14 EO | | | octyl | decyl | 14 | 18 |
| 11 | 2-Hydroxytetradecyl-hexyl ether + 14 EO | | | dodecyl | hexyl | 14 | 18 |
| 12 | 2-Hydroxyhexadecyl-ethyl ester + 13 EO | | | tetradecyl | ethyl | 13 | 16 |
| 13 | 2-Hydroxyoctadecyl-methyl ether | | | hexa- | | | |

TABLE I-continued

Formula 1 where y = 1 and x = 0

| Example | Active Substance | Hydroxyl number | Cloud point in °C | $R_1$ | $R_2$ | z | Carbon Atoms $R_1 + R_2$ |
|---|---|---|---|---|---|---|---|
| | + 14 EO | | | decyl | methyl | 14 | 17 |
| 14 | 2-Hydroxyoctadecyl-ethyl ether + 14 EO | | | hexadecyl | ethyl | 14 | 18 |

For the production of the technical ethoxylation products of Formula I, which may contain the ethoxylation product of Compound V (adduct of 2 mols of 1,2-epoxyalkane and 1 mol of alcohol) in minor quantities as by-product, the procedure as in the following example was adopted. In similar manner also the products listed in Table II were obtained.

EXAMPLE 15

2-Hydroxydecyl-butyl ether + 10 EO

As described in Example 1, 1 mol of 1,2-epoxydecane was caused to react with 5 times the molar quantity of n-butanol and 0.04 gm-atom of sodium. After distillation of the excess alcohol, the reaction with 10 mols of ethylene oxide was conducted in an autoclave under the conditions described in Example 1, except for the addition of the sodium methylate catalyst. The product thus obtained had a cloud point of 64°C.

TABLE II

| Example | Active Substance |
|---|---|
| 16 | 2-Hydroxydecyl-isobutyl ether + 10 EO (cloud point 67°C) |
| 17 | Reaction product of 1,2-epoxydecane with a $C_4$-oxo-alcohol isomer mixture + 10 EO |
| 18 | Reaction product of $C_{6-8}$ terminal epoxide with $C_{6-8}$ first distillate fatty alcohol + 10 EO |
| 19 | Reaction product of $C_{8-10}$ terminal epoxide with hexanol + 11 EO |
| 20 | Reaction product of $C_{8-10}$ terminal epoxide with 2-ethylhexanol + 12 EO |
| 21 | Reaction product of $C_{15-18}$ terminal epoxide with methanol + 13 EO |

The $C_{6-8}$ terminal epoxides, $C_{8-10}$ terminal epoxides and $C_{15-18}$ terminal epoxides were those obtained from the corresponding chain length terminal olefins which were derived from the cracking process.

EXAMPLE 22

Acid catalyzed condensation 256 gm (2 mol) of 1,2 -epoxy octane were added dropwise to a solution of 6.8 ml of a 50% boron trifluoride-etherate in 1020 gm (10 mol) of n-hexanol at 100°C. After the reaction ceased, the excess alcohol was distilled from the reaction product. 230 gm (1 mol) of the so-obtained reaction product, after neutralization of the boron trifluoride-etherate, was admixed with sodium methylate and reacted with 10 mols of ethylene oxide according to the procedure of Example 1. The ethoxylation product thus obtained had a cloud point of 58° to 62°C. The composition of the ethoxylation product was determined by MNR spectroscopy and through gas chromatography to be:

Ethoxylate of 2-hydroxyoctyl-hexylether
($x = 0$, $y = 1$ in Formula I) — 58%
Ethoxylate of 1-hydroxymethylheptyl-hexylether
($x = 1$, $y = 0$ in Formula I) — 42%.

EXAMPLE 23

Wash test in the launderometer

To determine the washing effect, the secondary alcohol ether ethoxylate of Formula I of the invention were tested by washing standardized soiled textiles as follows: unfinished cotton textile (C), finished cotton textile (FC), polyester/finished cotton textile (PFC), and polyester textile (P). The washing time including heating up time was 30 minutes: the water hardness, 16° German hardness (dH): the bath ratio, 1:12 for C, otherwise 1:30. The washing temperature varied according to the type of test fabric (see Table III). The washing tests were carried out with a washing agent of the following composition:

| % by weight | Ingredient |
|---|---|
| 3.0 | Secondary alcohol ether ethoxylate of Formula 1, |
| 7.0 | Sodium alkylbenzenesulfonate, |
| 3.5 | Soaps of predominantly $C_{18-20}$ fatty acids, |
| 40.0 | Sodium tripolyphosphate, |
| 3.5 | Waterglass, $Na_2O \cdot 3.3 SiO_2$, |
| 24.0 | Sodium perborate, |
| 0.2 | Ethylenediaminetetracetic acid, sodium salt, |
| 1.0 | Carboxymethylcellulose, sodium salt, |
| Balance | Sodium sulfate and water. |

As measure of the washing effect, the whiteness of the washed test fabrics was determined and expressed in the following Table III as "% Remission".

The comparative washing agent composition contained, in place of the ethoxylation products of Formula I, an equal amount by weight of a $C_{12}$ to $C_{18}$-coconut fatty alcohol + 10 EO, a known nonionic surface-active compound.

Table III in its entirety shows a clear increase in the washing effect by virtue of the employment of the compounds of Formula I in the washing agent composition. In accordance therewith the compounds of Formula I which, as indicated above, are prepared from short-chain alcohols that aren't useful for conventional manufacture of surface-active compounds, can be used with advantage in place of long-chain ethoxylated fatty alcohols.

TABLE III

| Washing agent containing a secondary alcohol ether ethoxylate according to example | Test fabric, washing temperature, washing agent, concentration in gm/liter. | | | | | | | |
|---|---|---|---|---|---|---|---|---|
| | "C"-90°C | | "FC"-60°C | | "PFC"-60°C | | "P"-40°C | |
| | 3.0 | 5.0 | 3.0 | 5.0 | 3.0 | 5.0 | 3.0 | 5.0 |
| Comparison | 52 | 81 | 47 | 62 | 47 | 67 | 49 | 58 |
| Example 2 | 55 | 81 | 52 | 64 | 52 | 68 | 50 | 59 |
| Example 1 | 55 | 81 | 53 | 64 | 52 | 68 | 50 | 58 |
| Example 7 | 55 | 81 | 53 | 64 | 54 | 67 | 49 | 58 |
| Example 15 | 55 | 81 | 52 | 64 | 51 | 68 | 50 | 58 |
| % Remission starting value | 45 | | 40 | | 36 | | 33 | |
| Maximum % remission | 86 | | 86 | | 84 | | 82 | |

The following Examples 24 to 28 of Table IV describe washing and cleaning agent compositions utilizing the new active substances of Formula I. The preparation of Example 24 is utilized as a full washing agent composition. That of Example 25 is utilized as a fine washing agent composition. That of Example 26 is utilized as a prewashing agent composition. That of Example 27 is utilized as a fluid washing agent composition and that of Example 28 is utilized as a powdery cleaning agent composition.

In the listing of compounds in the preparations of the Examples in Table IV, the abbreviations or designations have the following significance. The various compounds capable of forming salts are employed in the form of the sodium salt unless otherwise indicated.

"ABS"— the salt of alkylbenzenesulfonic acid with 10 to 15, preferably 11 to 13 carbon atoms, in the alkyl chain, obtained by condensation of straight-chain terminal olefins with benzene and sulfonation of the thus-formed alkylbenzene, "Alkanesulfonate"— a sulfonate obtained from paraffins with 12 to 16 carbon atoms by sulfoxidation, "Olefinsulfonate"— a sulfonate obtained from olefin mixtures with 12 to 18 carbon atoms by sulfonation with $SO_3$ and hydrolysis of the sulfonation product with aqueous sodium hydroxides. The olefinsulfonate consists substantially of alkenesulfonate and hydroxyalkanesulfonate, and contains, however, also a slight amount of alkanedisulfonates, "Fs-estersulfonate"— a sulfonate obtained from the methyl ester of a hardened tallow fatty acid, by sulfonation with $SO_3$, "CA-sulfate" or "TA-sulfate"— the salts of sulfated, substantially saturated fatty alcohols, prepared by reduction of coconut fatty acid or tallow fatty acid respectively, "CA-EO-sulfate"— the salt of the sulfated addition product of 2 mols of ethylene oxide to 1 mol of coconut fatty alcohol, "Soap"— the salts derived from fatty acid mixtures of an iodine number of 4, whose composition was 21% by weight of $C_{12}$, 8% by weight of $C_{14}$, 4% by weight of $C_{16}$, 22% by weight of $C_{18}$, 8% by weight of $C_{20}$, and 37% by weight of $C_{22}$, whereby the soap has a foam inhibiting effect due to the increased average carbon number, "Foam Inhibitor"— a mixture of about 45% of a N,N'-di-(alkylamino)-chlorotriazine and about 55% of a N,N',N''-tri-(alkylamino)-triazine, where the alkyls in their triazine derivatives are a mixture of homologs containing from 8 to 18 carbon atoms, "NTA" or "EDTA"— the salts of nitrilotriacetic acid or ethylenediaminetetraacetic acid, "Perborate"— a product of the approximate compositon $NaBO_2.H_2O_2.3\ H_2O$, containing about 10% of active oxygen, "CMC"— the salt of carboxymethylcellulose having a substitution degree of 0.7 to 0.8.

In place of the given compounds of Formula I indicated in Table IV, other described compounds of Formula I can be employed with comparable results.

TABLE IV

| Component | Washing agent composition components in % by weight for Examples | | | | |
|---|---|---|---|---|---|
| | 24 | 25 | 26 | 27 | 28 |
| ABS | — | 3.0 | 2.0 | — | 5.8 |
| Fs-estersulfonate | 7.0 | — | — | — | — |
| Alkanesulfonate | — | — | — | 4.0 | — |
| Olefinsulfonate | — | — | — | — | 1.0 |
| CA-EO-sulfate | — | 4.0 | — | — | 1.0 |
| Soap | 3.0 | 3.0 | — | — | 1.2 |
| Foam Inhibitor | 0.5 | — | — | — | — |
| Compound of Example 1 | — | — | — | 4.0 | — |
| Compound of Example 2 | 4.0 | — | 6.0 | — | 2.0 |
| Compound of Example 15 | — | 4.0 | 4.0 | — | — |
| $Na_5P_3O_{10}$ | 20.0 | 40.0 | 40.0 | — | 10.0 |
| NTA | 8.0 | — | — | — | — |
| $K_4P_2O_7$ | — | — | — | 16.0 | — |
| Potassium Toluenesulfonate | — | — | — | 4.0 | — |
| EDTA | 0.25 | — | 0.2 | — | — |
| Perborate | 28.0 | — | — | — | — |
| Waterglass 1 $Na_2O$: 3.3 $SiO_2$ | 3.0 | 3.0 | 4.5 | — | 5.0 |
| $Na_2CO_3$ | — | — | 5.0 | — | 39.5 |
| Sodium Sulfate | 5.0 | 38.0 | 32.0 | — | 26.0 |
| $MgSiO_3$ | 1.8 | — | — | — | — |
| CMC | 2.0 | 1.5 | 1.4 | — | — |

TABLE IV-continued

| Component | Washing agent composition components in % by weight for Examples | | | | |
|---|---|---|---|---|---|
| | 24 | 25 | 26 | 27 | 28 |
| Ethanol | — | — | — | 10.0 | — |
| Remainder, water, dyes, perfumes, optical brighteners | | | | | |

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. Secondary alcohol ether ethoxylates having the formula

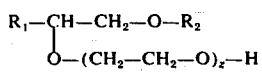

wherein $R_1$ is a straight-chain aliphatic hydrocarbon radical having from 4 to 18 carbon atoms selected from the group consisting of alkyl and alkenyl, $R_2$ is an aliphatic hydrocarbon radical having from 1 to 10 carbon atoms selected from the group consisting of alkyl and alkenyl, and $z$ is an average value between 3 and 18, with the proviso that the sum of the carbon atoms in $R_1$ and $R_2$ is from 6 to 22.

2. The secondary alcohol ether ethoxylates of claim 1 wherein $z$ is an average value from 5 to 15.

3. The secondary alcohol ether ethoxylates of claim 1 wherein $R_1$ and $R_2$ are alkyl and the sum of the carbon atoms in $R_1$ and $R_2$ is from 10 to 18.

4. The secondary alcohol ether ethoxylates of claim 3 wherein the $R_2$ alkyl is straight chained.

5. The secondary alcohol ether ethoxylates of claim 1 where $z$ is an average value from 5 to 15, $R_1$ is a straight-chained alkyl having 4 to 10 carbon atoms and $R_2$ is a straight-chained alkyl having 4 to 8 carbon atoms.

* * * * *

UNITED STATES PATENT OFFICE
CERTIFICATE OF CORRECTION

Patent No. 3,943,178            Dated March 9, 1976

Inventor(s) Werner Stein, Wolfgang Rupilius, Eric Sung and Peter Krings

It is certified that error appears in the above-identified patent and that said Letters Patent are hereby corrected as shown below:

1st Page, Col. 1, Item 75, line 3, after "Rhineland;" insert
-- ERIC SUNG, Monheim, Rhineland; --

| Column | Line | |
|---|---|---|
| 7 | 55 | "eleyl" should be -- oleyl --. |
| 12 | 49 | "bacteris" should be -- bacteria --. |

Signed and Sealed this

Fifteenth Day of February 1977

[SEAL]

Attest:

RUTH C. MASON
*Attesting Officer*

C. MARSHALL DANN
*Commissioner of Patents and Trademarks*